United States Patent [19]

Magistro

[11] Patent Number: 5,210,358

[45] Date of Patent: May 11, 1993

[54] CATALYST COMPOSITION AND PROCESS FOR THE PREPARATION OF ETHYLENE FROM ETHANE

[75] Inventor: Angelo J. Magistro, Brecksville, Ohio

[73] Assignee: The B.F. Goodrich Company, Akron, Ohio

[21] Appl. No.: 842,869

[22] Filed: Feb. 27, 1992

Related U.S. Application Data

[60] Division of Ser. No. 691,647, Apr. 25, 1991, Pat. No. 5,112,793, which is a continuation-in-part of Ser. No. 567,510, Aug. 15, 1990, abandoned.

[51] Int. Cl.$^5$ .......................... C07C 2/00; C07C 5/00; C07C 5/327; C07C 5/373
[52] U.S. Cl. .................... 585/500; 585/654; 585/657; 585/658; 585/661; 585/662; 585/663; 585/641; 585/642
[58] Field of Search ............... 585/500, 654, 657, 658, 585/661, 662, 663, 641, 642

[56] References Cited

U.S. PATENT DOCUMENTS

| | | | |
|---|---|---|---|
| 3,420,901 | 1/1969 | Schulz | 502/346 X |
| 4,100,211 | 7/1978 | Magistro | 502/303 X |
| 4,102,936 | 10/1978 | Magistro | 260/656 R |
| 4,119,570 | 10/1978 | Kroenke et al. | 502/304 X |

Primary Examiner—Patrick P. Garvin
Assistant Examiner—E. D. Irzinski
Attorney, Agent, or Firm—Joe A. Powell

[57] ABSTRACT

Solid solution catalyst in particulate form consisting of attrition resistant $\alpha$-Al$_2$O$_3$ particles with 0.5 to 10% by weight, expressed as the oxide, of iron cations substituted for aluminum cations in said catalyst support stabilized with 0.5 to 10% by weight, expressed as the oxide, of lanthanum and modified with at least two, preferably three, metal cations selected from the metals consisting of chromium, cobalt, magnesium, manganese, and barium; wherein one of said metal cations is barium and said catalyst has X-ray diffraction pattern with peak positions different than that of the $\alpha$-Al$_2$O$_3$ structure. A process is disclosed which produces ethylene from ethane while producing reduced amounts of vinyl chloride from said ethane to ethylene process.

23 Claims, 1 Drawing Sheet

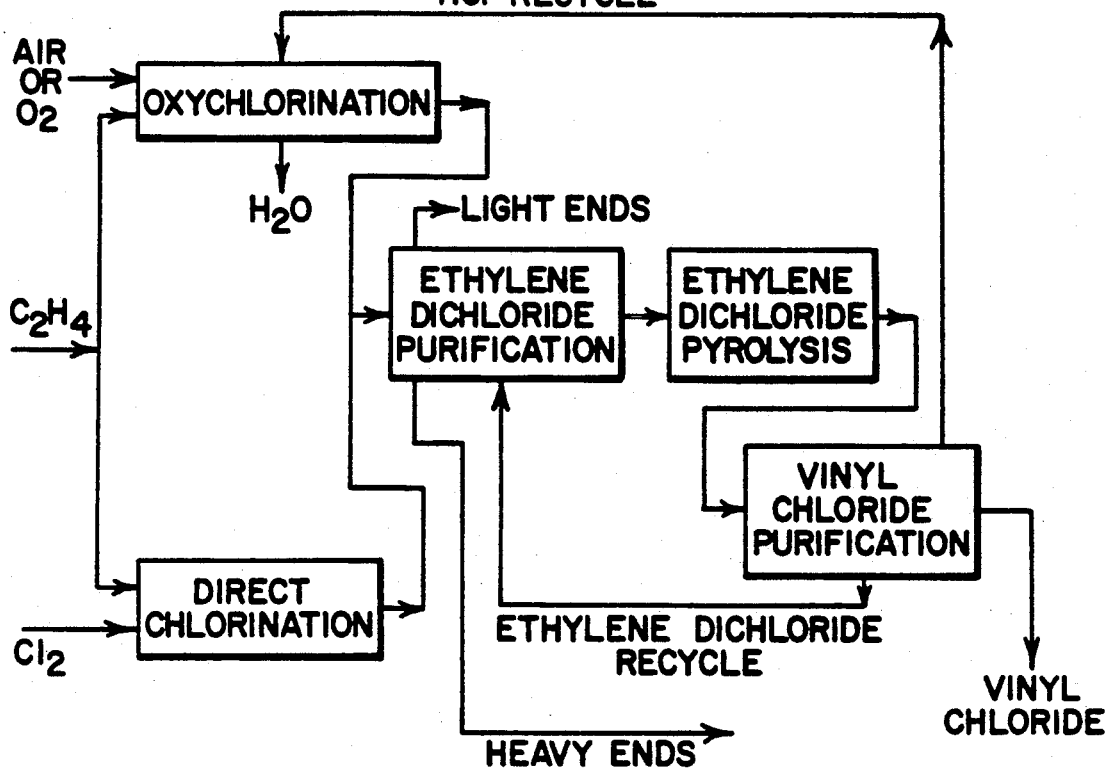
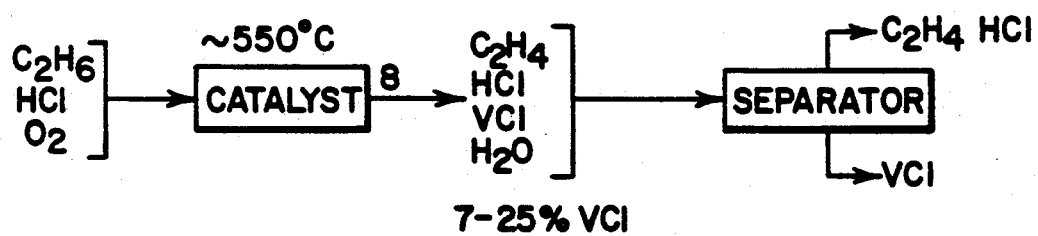
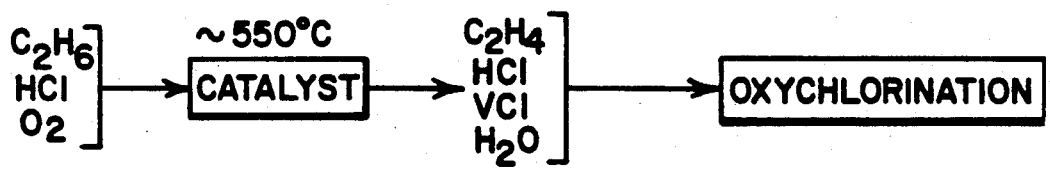

CATALYST COMPOSITION AND PROCESS FOR THE PREPARATION OF ETHYLENE FROM ETHANE

CROSS-REFERENCE TO RELATED APPLICATION

This is a division of parent application Ser. No. 07/691,647 filed on Apr. 25, 1991 and now U.S. Pat. No. 5,112,793 which is a continuation of application Ser. No. 07/567,510 filed 08/15/90 and now abandoned.

This application is a continuation-in-part of copending U.S. patent application Ser. No. 07/567,510 filed Aug. 15, 1990, now abandoned.

FIELD OF THE INVENTION

This invention relates to a catalyst for converting ethane to ethylene whereby the amount of vinyl chloride formed in the reaction is reduced. A process is disclosed which converts ethane to ethylene and the ethylene containing stream is subsequently fed to an oxychlorination process to convert the ethylene to ethylene dichloride.

BACKGROUND OF THE INVENTION

Vinyl chloride can be prepared using a number of well known processes. Two familiar processes are the hydrochlorination of acetylene and the oxychlorination of ethylene to form dichloroethane which in turn is dehydrohalogenated to form vinyl chloride, see U.S. Pat. No. 2,847,483. As acetylene is more expensive than ethylene, the latter process is economically favored and much activity is noted in this art area, see U.S. Pat. No's. 3,634,330; 3,454,663; 3,448,057; and 3,624,170. Ethylene, in turn, can be prepared by the oxydehydrogenation of ethane, see U.S. Pat. No. 3,769,362. In all processes, high yields of ethylene are particularly desired. In processes which use ethane as a feed stock in the presence of either chlorine or hydrogen chloride, they can produce not only ethylene but also can directly produce vinyl chloride and other valuable products such as ethylene dichloride, ethyl chloride, and the like. The ethylene, ethylene dichloride, and ethyl chloride can be readily reacted to form more vinyl chloride.

Preparation of vinyl chloride can be effected by the balanced vinyl chloride monomer (VCM) process, as described in the article entitled "Oxychlorination of Ethylene" by Messrs. Cowfer and Magistro in "Encyclopedia of Chem. Tech., 3rd Ed; Wiley; New York, 1983; Vol. 23, pp. 865–885. The balanced vinyl chloride monomer process is schematically illustrated in FIG. 1, herein.

In one proposed method in which ethylene is produced, ethane, a chlorine source and oxygen are passed through a reactor maintained at about 550° C. where fluidized solid solution catalyst is used to produce a stream from the reactor containing ethylene, hydrogen chloride, vinyl chloride and water. The amount of vinyl chloride in this stream, also identified as Stream A in the drawings, was in the range of 7-25% on molar efficiency basis; that is, 7-25 moles of vinyl chloride were produced for every 100 moles of ethane which were fed to the reactor. Stream A was fed into a separator where vinyl chloride was separated from ethylene and other constituents. Ethylene and other constituents were fed into the oxychlorination unit of FIG. 1 and the ethylene dichloride product was treated and subsequently produced vinyl chloride monomer, as outlined in FIG. 1.

A proposed process of using a separator to separate vinyl chloride from ethylene and other constituents is schematically depicted in FIG. 2. It would be desirable to produce ethylene from ethane whereby the amount of vinyl chloride produced would be minimized so as to reduce or eliminate the separation step thus allowing the product stream containing ethylene to be fed directly to an oxychlorination process unit.

SUMMARY OF THE INVENTION

This invention is directed to a solid solution catalyst which is used to convert ethane, a chlorine source such as hydrogen chloride, and oxygen to a stream containing ethylene, hydrogen chloride, vinyl chloride, carbon oxides, chlorinated by-products, and water wherein the objective is to minimize the amount of vinyl chloride and which stream does not have vinyl chloride removed but is passed directly into the oxychlorination unit and the ethylene dichloride product is treated and subsequently produces vinyl chloride. The catalyst comprises iron cations substituted for aluminum cations in a host lattice of attrition resistant $\alpha$-$Al_2O_3$ particles having an iron content of 0.1 to 20% by weight expressed as the oxide stabilized with a total lanthanide content of 0.1 to 20% by weight expressed as the oxide and modified with at least two, preferably more than two, metal cations selected from the metals consisting of cobalt, manganese, chromium, magnesium and barium, wherein barium must be present as one of the metal cations. Amount of each of the metals is 0.05 to 10%, preferably 0.1 to 3%, and more preferably 0.2 to 2% by weight, based on the weight of the catalyst, including the alumina.

DESCRIPTION OF THE DRAWINGS

FIG. 1 a flow diagram of the balanced vinyl chloride monomer/process where ethylene and chlorine are ultimately converted to vinyl chloride monomer;

FIG. 2 is a flow diagram of a process for reacting ethane, a chlorine source such as hydrogen chloride and oxygen to produce a stream, stream A, containing ethylene, hydrogen chloride, vinyl chloride and water vapor, passing the stream to a separator in order to separate vinyl chloride from a stream containing ethylene and hydrogen chloride; passing the stream containing ethylene and hydrogen chloride to the oxychlorination unit to produce ethylene dichloride and passing the ethylene dichloride to a pyrolysis unit to produce vinyl chloride and passing vinyl chloride to a vinyl chloride purification unit of the balanced vinyl chloride monomer process; and FIG. 3 is a process similar to the one depicted in FIG. 2 except that the resulting stream, stream B, from the reaction of ethane, a chlorine source and oxygen is conveyed directly to the oxychlorination unit of the balanced vinyl chloride monomer process without a separation of vinyl chloride.

DETAILED DESCRIPTION OF THE INVENTION

U.S. Pat. No. 4,158,645 describes a fluidized solid solution catalyst based on alpha alumina containing iron stabilized with lanthanum and/or lanthanides and modified with metal cations selected from lithium, cobalt, copper, magnesium, chromium, and manganese in amount of 0.1 to 5% by weight expressed as oxide. Such catalysts have improved selectivity for the formation of vinyl chloride and/or have increased catalyst life.

The catalysts described in the previous paragraph promote the reaction of ethane with hydrogen chloride and oxygen at about 550° C. to produce a gaseous stream, also referred to herein as Stream A, of ethylene, hydrogen chloride, vinyl chloride monomer, and water vapor. Amount of vinyl chloride in this stream or Stream A is in the range of 7 to 25 mole percent. This stream is then taken to a separator where vinyl chloride is separated from ethylene and hydrogen chloride. The separated vinyl chloride is then taken to the vinyl chloride purification unit shown in FIG. 1 where it is purified into vinyl chloride product. The separated ethylene and hydrogen chloride from the separator are taken to the oxychlorination unit of FIG. 1 where ethylene dichloride is produced in accordance with the following equation:

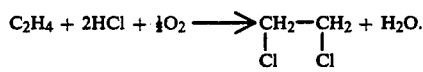

For the proposed new catalyst and process of this invention with no separation (FIG. 3) described in this patent, it is desired to minimize vinyl chloride in Stream B because unwanted ethylene trichloride (1,1,2-trichloroethane) is produced from vinyl chloride in the oxychlorination according to the following equation:

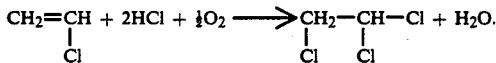

The trichloroethane by-product is undesirable and is combined with other chlorinated hydrocarbon by-products (light and heavy ends) for disposal. The above equation shows why it is desirable to minimize the amount of vinyl chloride in Stream B so that the amount of the trichloroethane by-product is correspondingly reduced. Disposal costs, and process economics, are strongly dependent on the amount of trichloroethane (1,1,2-trichloroethane) that is formed. Since the presence of trichloroethane is dependent on the presence of vinyl chloride in Stream B, it is desired to minimize the amount of vinyl chloride in Stream B thus reducing costs of the vinyl chloride process due to the reduced disposal costs.

The catalyst of this invention is effective in reducing the amount of vinyl chloride in Stream B to a level of less than about 5% yield on molar basis, preferably below 4%, more preferably below 3%, and especially below 2%. By reducing the amount of vinyl chloride, Stream B can be taken directly to the oxychlorination unit shown in FIG. 1 thus by-passing and doing away with the separator shown in FIG. 2. Reduced vinyl chloride formation in the ethane to ethylene process will cause less by-products from vinyl chloride monomer to be produced, therefore, reducing the cost of disposal. This will reduce process costs for disposal of unwanted by products from the oxychlorination process. This reduced vinyl chloride monomer allows the elimination of the need for a separator and, therefore, further lowers the overall process costs.

The catalyst of this invention is a solid solution catalyst based on alpha alumina containing iron stabilized with lanthanum and/or lanthanides and modified with at least two of select metals, preferably more than two of select metals. The solid solution catalysts of this invention can contain 0.1 to 20%, preferably 0.5 to 10%, by weight, of iron in the catalyst, expressed as iron oxide. The catalyst can contain similar levels of lanthanum and/or lanthanide, expressed as the oxide. The select metals include cobalt, manganese, chromium, magnesium, and barium, wherein barium must be present as one of the metals. The most preferred catalysts of this invention contain barium, cobalt, manganese, and chromium. The select metals are in the form of oxides or oxide precursors such as nitrates. Amount of each select metal in the catalyst, on oxide basis, is 0.05 to 10%, preferably 0.1 to 3%, and more preferably 0.2 to 2%, on weight basis of the catalyst, including the weight of the alumina catalyst support. Preferred catalysts of this invention are the following catalysts identified as (1), (2), (3) and (4):

(1) 4% $La_2O_3$, 2% $Fe_2O_3$, 0.5% $Cr_2O_3$, 0.5% CoO, 1.5% BaO;
(2) 4% $La_2O_3$, 2% $Fe_2O_3$, 0.5% $Cr_2O_3$, 0.5% CoO, 1.5% BaO, 1.0% MnO;
(3) 4% $La_2O_3$, 2% $Fe_2O_3$, 0.5% $Cr_2O_3$, 0.5% CoO, 1.5% BaO, 2.0% MnO.
(4) 4% $La_2O_3$, 2% $Fe_2O_3$, 0.5% CoO, 1% MnO, 1.5% BaO.

In the above catalysts, 4% $La_2O_3$ indicates weight percent of lanthanum oxide in the final catalyst which includes the weight of the alumina catalyst support. This applies to the other components in the catalyst disclosed in the disclosure herein, including the claims appended hereto.

In carrying out the reaction between ethane, a chlorine source, and oxygen using the catalyst of this invention, ethane is reacted with oxygen and the chlorine source in the presence of the solid solution particulate catalyst of this invention containing iron which is stabilized with lanthanum and/or lanthanides and modified with at least two selected metal cations, one of which must be barium, to prepare a stream, stream B, containing ethylene, vinyl chloride, hydrogen chloride, and water vapor. If vinyl chloride enters the oxychlorination unit, it is readily converted to 1,1,2-trichloroethane and this by-product component reduces the yield of desirable products and increases the by-product disposal capacity requirements. It is, therefore, desired to reduce production of vinyl chloride at this stage to below about 5% yield on molar basis, preferably below 4%, and especially below about 2%. When the vinyl chloride is reduced to the above level, it allows the removal of the separator and often results in a significant reduction in process cost. Depending upon feed and reactor conditions, conversion of ethane to products is 90 to 95% by mole, yield of ethylene is 85 to 90% by mole, and yield of the sum of ethylene and vinyl chloride is 85 to 90% on molar basis.

In the process, ethane, oxygen and a chlorine source are placed into a reactor vessel containing a solid solution catalyst of this invention. The process contemplates the use of standard techniques concerning the type of operation, reactor size and design, and the like. The process is conducted as a continuous process wherein reactants and products are continuously added and withdrawn. The solid solution catalyst can be fixed in a bed, it can be supported, or it can be present as particles that can readily fluidize during operation. A preferred embodiment of the process is to employ the solid solution catalyst in particulate form that will fluidize in the process thereby establishing maximum contact with the reactants. Such processes are known as fluid bed processes and the reactors designed for such are known as fluid bed reactors. A typical reactor is designed such that one or more gaseous reactants is introduced in the reactor below the catalyst bed and the gas pressurized through a support grid and suspends the catalyst in the reactor volume. Other reactants can be added at appropriate levels above, below, or any point in the fluid catalyst bed. Normally, products are withdrawn from the top portion of the reactor and collected or further treated as desired.

Although the process contemplates the use of known operating techniques and reaction conditions, certain conditions are herein stated as useful and practical. The reactants comprise ethane, oxygen, usually used in the form of air, and a chlorine source. The chlorine source is preferably hydrogen chloride gas. Using one mole of ethane as a basis, the hydrogen chloride is used at from about 0.1 mole to about 10 moles or more. More preferably, the hydrogen chloride is used at a level of from about 0.5 mole to 5 moles per mole of ethane. In general, as a higher ratio of hydrogen chloride to ethane is used, the yield of vinyl chloride and other chlorinated products increases and the yield of ethylene decreases. However, levels of use of hydrogen chloride above 5 moles per mole of ethane also increase the amount of hydrogen chloride to recycle. Excellent results have been obtained using about 1 to about 4 moles of hydrogen chloride per mole of ethane. As both ethylene and vinyl chloride can be prepared in significant amounts using the catalysts and as the yield of ethylene to vinyl chloride is highly dependent upon the hydrogen chloride to ethane ratio in the reactant feed, the process can be termed either an oxydehydrogenation process to prepare ethylene or an oxychlorination and pyrolysis process to prepare vinyl chloride.

Oxygen, preferably in the form of dry air, is used at from about 0.1 mole to about 1.5 moles of oxygen to one mole of ethane. A more preferred level is from about 0.5 mole to about 1 mole. The use of levels of oxygen of about 1 mole per mole of ethane is preferred in an oxychlorination process. In an oxydehydrogenation process, excellent results have been obtained using a level of oxygen of about 0.5 to 0.6 mole per mole of ethane.

Ethane, oxygen, and hydrogen chloride are passed into the reactor as reactants. Temperature of the reaction ranges from 400° C. to 650° C., and more preferably from 475° C. to 600° C. Materials withdrawn from the reactor in the product stream comprise ethylene, vinyl chloride, chlorinated products such as ethylene dichloride and ethyl chloride, carbon oxides (CO and $CO_2$), water, unreacted ethane and hydrogen chloride.

The improved feature in the oxydehydrogenation process described herein is the use of a solid solution catalyst containing iron cations substituted for cations in the host alumina lattice which catalyst is stabilized with lanthanum and/or lanthanides and modified with at least two selected metal cations, one of which must be barium. See U.S. Pat. No. 4,158,645 for a disclosure of a similar catalyst without barium. The catalyst is basically a solid solution of iron cations in a host alumina lattice. This is in contrast to catalysts wherein an active ingredient such as cupric chloride or iron oxide is merely adsorbed onto the surface of a support structure or material. The difference is crucial and can be distinguished in the physical state of the catalyst, in the activity of the catalyst, and in the life of the catalyst.

The solid solution catalyst is a true solution wherein iron cations are substituted for host lattice ions in the catalyst structure. An X-ray diffraction pattern of a solid solution catalyst is characteristic of the diffraction pattern of the host lattice. For example, a solid solution catalyst of $Fe_2O_3$ in $\alpha$-$Al_2O_3$.

A distinguishing feature of the solid solution catalysts of this invention, i.e., solid solution catalysts containing iron and stabilized with lanthanum and/or lanthanides and modified with at least two select metal cations, one of which must be barium, is in the increased selectivity and/or retention of iron by the catalyst upon use and reduction of vinyl chloride in Stream B. For example, an $\alpha$-$Al_2O_3$ solid solution catalyst containing iron cations which is stabilized with lanthanum cations and modified with at least two metals, one of which must be barium, preferably at least three metals, one of which must be barium, used at reaction conditions of 1 mole ethane/0.6 mole oxygen/1.5 mole hydrogen chloride, lost about 0.2% by weight of its original iron content after over 100 hours of use. In contrast, a catalyst which is a solid solution of iron in $\alpha$-$Al_2O_3$ stabilized with lanthanum but not modified lost about 3% of its original iron content after about 100 hours of use at the same set of conditions. In further contrast, a catalyst consisting of a simple solid solution of iron in $\alpha$-$Al_2O_3$ lost about 4% by weight of its iron content under the same conditions. In yet further contrast, a catalyst comprised of ferric oxide merely absorbed onto $Al_2O_3$, operating under the same set of conditions, lost over 8% by weight of its original iron content after about 100 hours of use.

The catalysts of this invention can also be prepared from attrition resistant catalyst supports. See U.S. Pat. No. 5,008,225 issued Apr. 16, 1991, for description of the attrition resistant catalyst supports. The attrition resistant catalyst support, when viewed under the electron microscope at 1000×magnification, readily shows that the alpha-alumina of the attrition resistant catalyst support mainly consists of non-aggregated or non-agglomerated particles that are substantially free of crystalline boundaries. Since the particles are devoid of crystalline grain boundaries, they are resistant to attrition. Aluminas of the attrition resistant alpha-alumina supports contain no surface crystalline grain boundaries. In order to have a low attrition alpha-alumina catalyst support, the final support should be substantially devoid of any crystalline grain boundaries, fractures or cracks and should not consist of an aggregation or agglomeration of the particles. The attrition resistant catalyst support is prepared in the same way as the alumina catalyst support but has lower attrition due to formation of a surface with no crystalline grain boundaries during processing.

Attrition resistance also depends on the physical form of the particles. Spheroidal particles with smooth surfaces will have lower attrition losses than particles with irregular shapes and rough edges. The term spheroidal also is meant to include spherical, elliptical, oblong, globular, and the like, so long as there are no irregular or sharp edges that are prone to attrition during handling or fluidization. The attrition resistant catalyst support is an inert substrate of alpha-alumina wherein the alpha-alumina particles are devoid or substantially devoid of any fractures, cracks or crystalline grain boundaries and have attrition number not exceeding 30, preferably not exceeding 15, more preferably not exceeding 10, especially not exceeding 5, and is thermally stable up to about 1000° C. The attrition number is described in U.S. Pat. No. 5,008,225.

Solid solution catalysts containing iron cations can be of different types. The iron exists as ferric ($Fe^{+3}$) ions. The ferric ion is the active ion in the catalyst. However, since ferrous ion can oxidize to a ferric ion in the process, the use of solid solution catalysts containing ferrous ions is within the scope of this invention.

In the solid solution catalyst containing iron cations there is direct substitution of iron ions for host lattice ions. An example of this catalyst is ($Fe_x^{+3}M_{2-x}^{+3}$)$O_3$ wherein x is greater than 0 and less than 2 and M is a metal such as aluminum or chromium. An example of this is a solid solution catalyst of ferric oxide ($Fe_2O_3$) in aluminum oxide ($Al_2O_3$). As the ferric ion is much greater in size than an aluminum $+3$ ion, the solubility of the ferric ion in aluminum oxide is limited. Hence, the solid solution catalysts of the example wherein M is aluminum encompass materials of the formula wherein x has an upper limit of about 0.15.

The solid solution catalyst containing iron is stabilized with lanthanum and/or a lanthanide. Although the lanthanum or lanthanide is an integral part of the catalyst, it is believed that the lanthanum or lanthanide does not enter into solid solution with the host lattice as does the iron. Characterization of the catalysts of this invention will be discussed further in a subsequent section of this specification.

The lanthanum and lanthanides can be employed in the solid solution catalysts singly or as mixtures of the metals. The lanthanides are elements 57 to 71 of the Periodic Table. More preferably, the lanthanides used are lanthanum, cerium, praseodymium, neodymium, and erbium. Excellent results have been obtained using a catalyst of $Fe_2O_3$ in $\alpha$-$Al_2O_3$ stabilized with lanthanum.

The solid solution catalyst containing iron and stabilized with lanthanum or a lanthanide is further modified with at least two select metal cations, one of which must be barium. The use of these cations results in a catalyst which reduces the amount of vinyl chloride in the product stream from the reaction of ethane, oxygen and a chlorine source and/or increased catalyst lifetime. The metal cations employed are selected from the group consisting of barium, chromium, manganese, magnesium, and cobalt, wherein barium must be present.

Although the selected metal cations are an integral part of the catalyst, it is believed that the selected metals do not enter into solid solution with the host lattice as does the iron.

The solid solution catalysts of this invention contain iron and have X-ray diffraction patterns characteristic of the host lattice material. The catalyst is first identified and characterized by analyzing it to determine what elements it contains. This can be done using well known techniques such as chemical analysis, atomic absorption spectroscopy, X-ray fluorescence spectroscopy, and optical microscopy. For example, the solid solution catalyst of iron oxide in aluminum oxide, stabilized with lanthanum and modified with cobalt and barium, would show iron, lanthanum, aluminum, cobalt, barium, and oxygen to be present in the catalyst. The presence and quantity of iron in the catalyst can be readily determined using a standard method of chemical analysis such as the dichromate method for the determination of iron. The amount of iron in the solid solution catalysts is limited by the solubility of the ions in the host lattice. Presence of alumina, cobalt, manganese, magnesium, chromium, and barium can be determined by X-ray fluorescence.

The second step of identification and characterization involves running an X-ray diffraction scan on the catalyst. The X-ray diffraction scan will show a pattern of peaks, which peaks have positions and intensities distinctive of the crystalline phases which are present. The X-ray diffraction peak positions and intensities of the catalyst can be compared to peak positions and intensities of known crystalline phases that are published in the ASTM Powder Diffraction File, for example, or that are experimentally obtained. For example, a catalyst comprised of iron oxide merely impregnated on aluminum oxide will have an X-ray diffraction pattern of peak positions showing the distinct peak positions and intensities of iron oxide and aluminum oxide crystalline phases.

In contrast, the X-ray diffraction pattern of a solid solution catalyst containing iron shows the positions of the X-ray diffraction peaks in the solid solution catalyst to be shifted from the peak positions in the X-ray diffraction pattern of the host lattice. The shift in peak positions may be accompanied by changes in the relative intensities of the peaks, but the intensity changes are generally small.

The shift in X-ray diffraction peak positions when solid solutions are formed results from the expansion or contraction of the dimensions of the unit cell of the crystalline phase of the host lattice. The dimensions of the unit cell of the host lattice are changed due to the substitution of iron cations for cations of the host lattice. If the cation is larger than the cation it displaces, the unit cell dimensions will increase in size to accommodate the larger cation. The amount of expansion or contraction, if the iron cation is smaller than the host lattice cation it displaces, of the unit cell dimensions can be determined by calculating the lattice parameters of the unit cell of the solid solution phase and comparing these lattice parameters to the lattice parameters of the unit cell of the host. A change in lattice parameters due to iron substitution in a crystalline host lattice is frequently in accordance with Vegard's law. Since a change in the lattice parameters causes a change in the X-ray diffraction peak positions, a quick comparison of the X-ray diffraction pattern of the catalyst and the pattern of the host lattice will show whether a solid solution catalyst has been prepared.

Alternately, a more accurate method of confirming the preparation of a solid solution catalyst is to experimentally run X-ray diffraction scans of the prepared catalyst and of the host lattice and then calculate the lattice parameters of each. If the values obtained for the lattice parameters of the catalyst and host lattice are different, a solid solution catalyst has been prepared. If the geometry and dimensions, i.e., lattice parameters, of the unit cell of the host lattice is now known, it can be determined using established methods for indexing and interpreting X-ray diffraction patterns. The high $2\theta$ values (where $\theta$ is the Bragg angle) are normally used to calculate the lattice parameters.

In the case of a solid solution catalyst stabilized with lanthanum and/or a lanthanide and modified with at least two selected metals, the X-ray diffraction pattern will clearly show the presence of the solid solution, which is the primary crystalline phase, and will additionally show the presence of crystalline lanthanum and/or lanthanide and selected metal compounds which are present in detectable amounts. For example, in the case of a solid solution catalyst of $Fe_2O_3$ in $\alpha\text{-}Al_2O_3$ stabilized with lanthanum and modified with cobalt and barium, the X-ray diffraction pattern will show the presence of the $Fe_2O_3$ in $\alpha\text{-}Al_2O_3$ solid solution crystalline phase, the crystalline compounds of lanthanum such as $La_2O_3$ and $LaAlO_3$, crystalline cobalt oxide, and crystalline barium oxide.

In summary, the solid solution catalysts of this invention can be identified and characterized by (1) the presence of iron, lanthanum and/or lanthanides, and the selected metals in the catalyst and (2) the X-ray diffraction pattern of the catalyst. The iron is present as cations substituted in the host lattice for cations of the host lattice. The iron content can be measured using standard analysis techniques. The X-ray diffraction pattern of the solid solution catalyst will exhibit peak positions characteristic of the host lattice but shifted due to the presence of the iron cations in the host lattice. Lattice parameters calculated for the host lattice and the solid solution catalyst will differ. The X-ray diffraction pattern of the solid solution catalysts of this invention will exhibit extraneous peaks in the pattern due to formation of crystalline compounds other than the solid solution catalyst itself, such as lanthanum oxide or lanthanide oxides, and selected metal oxides.

The solid solution catalysts used in the examples were prepared by first impregnating a host lattice precursor with an iron salt, a lanthanum salt and selected metal salts or precursors that yield the oxides upon heating, then heating the impregnated host lattice precursor to about 550° C. followed by heating to 1200° C. or more. The catalyst prepared is a solid solution catalyst containing iron, stabilized with lanthanum and/or lanthanides and modified with the selected metals. The catalyst has a distinctive X-ray diffraction pattern.

The solid solution catalyst can also be prepared in other ways. Another method is to physically admix iron oxide, lanthanum or a lanthanide oxide, the selected metal oxides, and the host lattice material and heat the mix to allow dissolution and substitution of the iron ions for those of the host lattice, and formation of the stabilized and modified catalyst. Heating conditions vary due to the nature of the host lattice employed but typically are above about 1100° C.

A third method of preparation is to use the so-called sol-gel process wherein an iron salt, lanthanum and/or lanthanide salt, selected metal salts and a salt precursor of the host lattice are mixed together as solutions and a base is added to co-precipitate out a mixture of the corresponding hydrated oxides. The mix is then heated to above about 1100° C. to effect dissolution and substitution of the iron ions for aluminum ions.

A fourth method involves the dissolution of selected metal salts in a solvent such as water or ethanol and the use of the solution to impregnate a preformed solid solution catalyst already stabilized with lanthanum and/or lanthanides. The mix is then dried and heated to cause the metal salts to decompose upon heating to yield the oxides.

In all of these methods, a metal oxide precursor can be used in place of the metal oxide per se. The precursor, which is typically a salt of the metal, decomposes on heating to yield the oxide form of the metal. Examples of iron oxide precursors are iron chloride, iron sulfate, iron formate, iron oxalate, iron citrate, iron nitrate, and the like. Precursors of the oxides of lanthanum or lanthanides and of the selected metals can also be employed. Examples of lanthanum oxide precursors are lanthanum nitrate, lanthanum chloride, lanthanum sulfate, lanthanum oxalate, and the like. Examples of selected metal oxide precursors are chromium acetylacetonate, chromium nitrate, chromium chloride, manganese chloride, manganese oxalate, manganese nitrate, cobalt chloride, cobalt nitrate, cobalt oxalate, barium nitrate, and barium chloride, and barium carbonate, magnesium chloride and magnesium nitrate.

The solid solution catalysts of this invention can be used in the process in the form of a fixed bed, a fluidized bed, on a fixed support, on a fluidized support, or in a number of ways well known to the art. Although in the examples the process used is a fluidized bed process, it is understood that other well known techniques can be employed. The following Examples are given to further illustrate the invention.

EXAMPLES

Solid solution catalysts were used to react ethane, oxygen and hydrogen chloride to ethylene, hydrogen chloride, vinyl chloride and steam. The reactions were conducted in a fluid bed reactor wherein the ethane, oxygen or oxygen used in the form of air, and anhydrous hydrogen chloride were premixed at a set molar ratio of reactants and the mixture fed into a heated reactor near the bottom. The catalyst used was in the form of particles of a size passing between 80 mesh and 325 mesh screens. Contact times in the reaction were from about 4 seconds to about 10 seconds. Products were withdrawn from the top of the reactor as gases, scrubbed with water and analyzed using a gas chromatograph. The process was run as a continuous process for times of 1 hour up to 300 hours or more per run.

The following examples detail experiments conducted using various mole ratios of reactants, various temperatures and times of reaction, and different solid solution catalysts.

EXAMPLE 1

This example demonstrates a solid solution catalyst containing the selected metals of chromium, cobalt, manganese and barium on an attrition resistant support.

A mixture of $La(NO_3)_3.6H_2O$ (34.37 gr), $Fe(NO_3)_3.9H_2O$ (31.9 gr), $Cr(NO_3)_3.9H_2O$ (7.28 gr), $Co(NO_3)_2.6H_2O$ (5.81 g), $Mn(NO_3)_2.6H_2O$ (5.51 gr), and $Ba(NO_3)_2$ (7.50 gr) dissolved in distilled water was slowly added to 297.4 gr of particulate attrition resistant gamma $Al_2O_3$ catalyst support with stirring to insure homogeneous mixing of solution with the catalyst support. The catalyst then was dried on a steam bath and then air dried overnight at 80° C. The dried catalyst was then calcined at 550° C. for 16 hours and then calcined at 1250° C. for 16 hours. The resulting catalyst was sieved to remove fines and used as is.

EXAMPLE 2

This example demonstrates the use of various solid solutions on an attrition resistant support catalyst of this invention as shown in Table A below in a reactor to promote the reaction of ethane, hydrogen chloride and oxygen, in the form of air, to ethylene, hydrogen chloride, vinyl chloride and steam. The reaction temperature was 550° C., contact time with fluidized catalyst was 12 seconds, and volume ratio of the reactants, i.e., ethane, hydrogen chloride and oxygen was respectively 1/1.75/0.7. The gaseous product Stream B was analyzed for the presence of vinyl chloride (VCM and the following results were obtained:

TABLE A

| % La | % Fe | % Cr | % Co | % Mn | % Ba | % VCM |
|------|------|------|------|------|------|-------|
| —    | 2.0  | —    | —    | —    | —    | 7.1   |
| 4.0  | 2.0  | 0.5  | —    | —    | —    | 6.6   |
| 4.0  | 2.0  | —    | 0.5  | —    | —    | 5.7   |
| 4.0  | 2.0  | —    | —    | —    | 2.9  | 4.6   |
| 4.0  | 2.0  | —    | 0.5  | —    | 2.9  | 4.5   |
| 4.0  | 2.0  | —    | —    | 0.5  | —    | 5.5   |
| 4.0  | 2.0  | 0.5  | 0.5  | —    | 1.5  | 4.4   |
| 4.0  | 2.0  | 0.5  | 0.5  | —    | 1.5  | 4.4   |
| 4.0  | 2.0  | —    | 0.5  | —    | 1.5  | 5.1   |
| 4.0  | 2.0  | 0.5  | 0.5  | 1.0  | 1.5  | 4.3   |
| 4.0  | 2.0  | 0.5  | 0.5  | 2.0  | 1.5  | 3.7   |
| 4.0  | 2.0  | —    | 1.0  | —    | 1.5  | 5.0   |
| 4.0  | 2.0  | —    | 1.0  | —    | 2.9  | 4.6   |
| 4.0  | 2.0  | —    | —    | 2.0  | 1.5  | 5.7   |
| 7.0  | 2.0  | —    | 1.0  | 2.0  | 1.5  | 4.2   |
| 4.0  | 2.0  | —    | 0.5  | 1.0  | 1.5  | 4.3   |
| 4.0  | 2.0  | 1.0  | 1.0  | 2.0  | 1.5  | 3.9   |
| 7.0  | 3.0  | —    | 1.0  | 2.0  | —    | 4.5   |
| 7.0  | 3.0  | —    | 1.0  | .5   | 1.5  | 4.5   |

The above results indicate that vinyl chloride monomer in Stream B can be reduced substantially by the use of the solid solution catalyst of this invention. The presence of barium in the catalyst is shown above to reduce the formation of vinyl chloride.

In the above table, percent of the metal refers to weight percent of that particular metal in the solid solution catalyst and percent of vinyl chloride monomer (VCM) refers to the number of moles of vinyl chloride formed in the reaction for every 100 moles of ethane fed to the reactor. As earlier described, the metals are in the form of oxides. For instance, 2.0% Fe given in the above table, means 2.0% by weight of ferric oxide ($Fe_2O_3$) and 1.0% Mn is 1.0% by weight of manganese oxide.

I claim:

1. An oxydehydrogenation process for producing ethylene from ethane comprising reacting 1 mole of ethane, 0.1 to about 1.5 moles of oxygen, and 0.1 to about 10 moles of hydrogen chloride at a temperature of from 400° C. to 650° C. in the presence of a solid solution catalyst such that said ethane is dehydrogenated to form ethylene and less than 5 moles of vinyl chloride is formed per 100 moles of ethane feed and wherein said solid solution catalyst comprises $\alpha$-$Al_2O_3$ catalyst support particles with iron cations substituted for aluminum cations in the host lattice of $\alpha$-$Al_2O_3$ catalyst support having an iron content of 0.1 to 20% by weight expressed as the oxide stabilized with a total lanthanide content of 0.1 to 20% by weight expressed as the oxide and modified with at least two metal cations selected from the group consisting of barium, cobalt, chromium, magnesium and manganese, wherein barium is one of said metal cations and wherein said metal cations are present in amounts of 0.05 to 10% of each metal by weight expressed as the oxide; wherein said lanthanide content expressed as the oxide is selected from oxides of the elements 57 to 71 of the Periodic Table, and mixtures thereof; said solid solution catalyst having X-ray diffraction pattern having peak positions different than that of the host lattice.

2. A process of claim 1 wherein the iron content of said catalyst is 0.5 to 10% by weight, expressed as the oxide, stabilized with 0.5 to 10% by weight, expressed as the oxide, of lanthanum.

3. A process of claim 2 wherein said catalyst is modified with 0.1 to 3% of each by weight of cobalt oxide and barium oxide.

4. A process of claim 2 wherein said solid solution catalyst comprises iron cations in said $\alpha$-$Al_2O_3$ host lattice stabilized with lanthanum oxide and modified with 0.1 to 3% of each by weight of chromium oxide, cobalt oxide, and barium oxide.

5. A process of claim 2 wherein said solid solution catalyst comprises iron cations in said $\alpha$-$Al_2O_3$ host lattice stabilized with lanthanum oxide and modified with 0.1 to 3% of each by weight of manganese oxide and barium oxide.

6. A process of claim 2 wherein said solid solution catalyst comprises iron in said $\alpha$-$Al_2O_3$ host lattice stabilized with lanthanum oxide and modified with 0.1 to 3% of each by weight of chromium oxide, cobalt oxide, manganese oxide, and barium oxide.

7. A process of claim 2 wherein said solid solution catalyst comprises iron in said $\alpha$-$Al_2O_3$ host lattice stabilized with lanthanum oxide and modified with 0.1 to 3% of each by weight of cobalt oxide and manganese oxide.

8. An oxydehydrogenation process for producing ethylene from ethane comprising reaction 1 mole of ethane, 0.1 to about 1.5 moles of oxygen and 0.1 to about 10 moles of hydrogen chloride at a temperature of from 400° C. to 650° C. in the presence of a solid solution catalyst such that said ethane is dehydrogenated to form ethylene and less than 5 moles of vinyl chloride is formed per 100 moles of ethane feed and wherein said solid solution catalyst comprises iron cations substituted for aluminum cations in a host lattice of $\alpha$-$Al_2O_3$ having iron content of 0.5 to 10% by weight expressed as the oxide stabilized with lanthanum oxide in amount of 0.5 to 10% by weight and modified with at least two metal cations selected from the metals consisting of chromium, cobalt, manganese, magnesium and barium in amount of 0.1 to 3% by weight of each metal expressed as the oxide, wherein barium is one of said metal cations and said catalyst having X-ray diffraction pattern having peak positions different than that of the host lattice.

9. A process of claim 8 wherein the amount of each said metal in said catalyst is expressed as the oxide is 0.2 to 2% by weight.

10. A process of claim 1 wherein said $\alpha$-$Al_2O_3$ catalyst support particles are substantially devoid of crystalline grain boundaries, cracks and fractures and having low attrition number, as determined by the roller attrition test.

11. A process of claim 10 wherein said solid solution catalyst is fluidizable, and is in the form of spheroidal particles, and has an attrition number not exceeding 30, and is thermally stable up to about 1000° C.

12. A process of claim 11 wherein said solid solution catalyst contains at least three metal cations and one of said metal cations is barium.

13. A process of claim 12 wherein said solid solution catalyst of claim 12 disposed on attrition resistant particulate $\alpha$-$Al_2O_3$ catalyst support passing between 80 mesh and 325 mesh screens being substantially devoid of crystalline grain boundaries, cracks and fractures with attrition number not exceeding 5 and consisting of the following components in the indicated weight amounts:
 (1) 4% $La_2O_3$, 2% $Fe_2O_3$, 0.5% $Cr_2O_3$, 0.5% CoO, 1.5% BaO;
 (2) 4% $La_2O_3$, 2% $Fe_2O_3$, 0.5% $Cr_2O_3$, 0.5% CoO, 1.5% BaO, 1.0% MnO;
 (3) 4% $La_2O_3$, 2% $Fe_2O_3$, 0.5% $Cr_2O_3$, 0.5% CoO, 1.5% BaO, 2.0% MnO.

(4) 4% $La_2O_3$, 2% $Fe_2O_3$, 0.5% CoO, 1% MnO, 1.5% BaO.

14. A process of claim 10 wherein the iron content of said catalyst is 0.5 to 10% by weight, expressed as the oxide, stabilized with 0.5 to 10% by weight, expressed as the oxide, of lanthanum.

15. A process of claim 10 wherein said solid solution catalyst is modified with 0.1 to 3% of each by weight of cobalt oxide and barium oxide.

16. A process of claim 10 wherein said solid solution catalyst comprises iron cations in said $\alpha$-$Al_2O_3$ host lattice stabilized with lanthanum oxide and modified with 0.1 to 3% of each by weight of chromium oxide, cobalt oxide, and barium oxide.

17. A process of claim 10 wherein said solid solution catalyst comprises iron cations in said $\alpha$-$Al_2O_3$ host lattice stabilized with lanthanum oxide and modified with 0.1 to 3% of each by weight of manganese oxide and barium oxide.

18. A process of claim 10 wherein said solid solution catalyst comprises iron in said $\alpha$-$Al_2O_3$ host lattice stabilized with lanthanum oxide and modified with 0.1 to 3% of each by weight of chromium oxide, cobalt oxide, manganese oxide, and barium oxide.

19. A process of claim 10 wherein said solid solution catalyst comprises iron in said $\alpha$-$Al_2O_3$ host lattice stabilized with lanthanum oxide and modified with 0.1 to 3% of each by weight of cobalt oxide, manganese oxide and barium oxide.

20. A process of claim 10 wherein the amount of each said metal in said catalyst is expressed as the oxide is 0.2 to 2% by weight.

21. A process of claim 1 wherein said reaction is conducted at a temperature of from about 475° C. to about 600° C.

22. A process of claim 1 wherein the molar amounts of hydrogen chloride is from about 0.5 mole to about 5.0 moles and the molar amounts of oxygen is from about 0.5 mole to about 1.0 mole, based on 1.0 mole of ethane.

23. A process of claim 1 wherein the product from said process is fed directly to an oxychlorination process.

* * * * *